US012617741B2

(12) United States Patent
Rivas Bascón et al.

(10) Patent No.: US 12,617,741 B2
(45) Date of Patent: May 5, 2026

(54) METHOD FOR THE MANUFACTURE OF α,β-UNSATURATED KETONES

(71) Applicant: SYMRISE AG, Holzminden (DE)

(72) Inventors: Nazaret Rivas Bascón, Granada (ES); Ricardo Rodriguez Ferrol, Granada (ES); Antonio Ruiz Sanchez, Granada (ES)

(73) Assignee: SYMRISE AG, Holzminden (DE)

( * ) Notice: Subject to any disclaimer, the term of this patent is extended or adjusted under 35 U.S.C. 154(b) by 419 days.

(21) Appl. No.: 17/919,785

(22) PCT Filed: Apr. 12, 2021

(86) PCT No.: PCT/EP2021/059417
§ 371 (c)(1),
(2) Date: Oct. 19, 2022

(87) PCT Pub. No.: WO2021/213828
PCT Pub. Date: Oct. 28, 2021

(65) Prior Publication Data

US 2023/0150907 A1 May 18, 2023

(30) Foreign Application Priority Data

Apr. 22, 2020 (EP) .................................... 20382329

(51) Int. Cl.
*C07C 45/34* (2006.01)

(52) U.S. Cl.
CPC .................................. *C07C 45/34* (2013.01)

(58) Field of Classification Search
CPC ..................................................... C07C 45/34
See application file for complete search history.

(56) References Cited

U.S. PATENT DOCUMENTS

| | | | | |
|---|---|---|---|---|
| 6,232,258 B1 * | 5/2001 | Ishii | C07C 45/34 502/155 | |
| 6,939,993 B2 * | 9/2005 | Sugahara | C07C 45/80 548/545 | |

FOREIGN PATENT DOCUMENTS

| | | | |
|---|---|---|---|
| EP | 1164131 | A1 | 12/2001 |
| EP | 1331215 | A1 | 7/2003 |

* cited by examiner

*Primary Examiner* — Sikarl A Witherspoon
(74) *Attorney, Agent, or Firm* — Dilworth & Barrese, LLP

(57) ABSTRACT

A method for the manufacture of an α,β-unsaturated ketone, which method comprises oxidizing an alkene having $—CH_2—$ adjacent a carbon-carbon double bond to α,β-unsaturated ketone by passing air or oxygen through a solution of the hydrocarbon containing a catalyst consisting of N-hydroxyphthalimide (NHPI) and cobalt diacetate tetrahydrate at standard temperature and pressure during a period of at least 12 hours.

13 Claims, 1 Drawing Sheet

(+)-Valencene (+)-Nootkatone

METHOD FOR THE MANUFACTURE OF α,β-UNSATURATED KETONES

Figure 1:
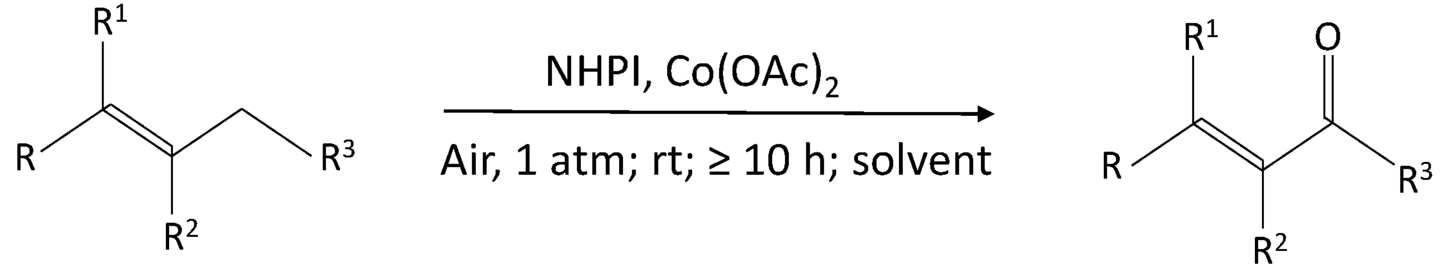

The present invention is concerned with a method for the manufacture of α,β-unsaturated ketones (enones) by oxidation of alkenes. The method is suitable for use as an industrial process and has particular utility for the manufacture of α,β-unsaturated ketones of interest in the field of fragrances.

The allylic oxidation of alkenes to enones is a chemical conversion that offers a direct route to high value products from chemical compounds which are readily available as bulk chemicals or otherwise obtained from renewable sources.

Accordingly, the allylic oxidation of alkenes to enones has found widespread use for the preparation of agricultural, pharmaceutical and flavoring products. A wide variety of methods have been used (and are reviewed by Weidmann, V. and Maison, W. in "Allylic Oxidations of Olefins to Enones", Synthesis 2013, 45 2201-2221).

Amongst these, the most commonly used method for allylic oxidation of alkenes to enones involves the use of stoichiometric amounts of chromium (VI) reagents such as chromium (VI) oxide, t-butyl chromate, sodium chromate, sodium dichromate and complexes comprising chromium (VI) oxide (for example, with pyridines, pyrazoles or benzotriazoles).

However, the method is complicated by a need for harsh reaction conditions to achieve acceptable conversion within suitable timescales and by difficulty in removing the chromium (VI) reagents from crude reaction product(s).

Furthermore, the method is not particularly suitable for an industrial process because of the amounts of chromium (VI) reagents involved and environmental regulations restricting chromium-containing waste chemicals.

Accordingly, industrial chemists have sought alternative methods for the allylic oxidation of alkenes to enones. These methods rely upon the use of a catalytic amount of chromium (VI) salt and/or other metal salt with stoichiometric amounts of oxidants such as t-butyl hydroperoxide, sodium perborate, potassium hydrogen persulfate.

However, the catalytic methods tend not to offer a significant improvement over the stoichiometric methods. The need for harsh reaction conditions often remains as does the difficulty in removing the chromium (VI) salt and/or other metal salt from crude reaction products.

Further, the catalytic methods do not lend themselves to an industrial process because the amounts of catalyst used tend to be high and challenge compliance with environmental regulations restricting chromium- or other metal-containing containing waste chemicals.

NHPI is known to catalyze the oxidation of alkanes to a variety of oxygen-containing compounds, including alcohols, ketones and carboxylic acids, under relatively mild conditions.

The NHPI catalyzed oxidation of alkanes generally requires heating to temperatures higher than 70° C. in the presence of oxygen at atmospheric pressure and one or more a metal co-catalyst, usually a cobalt (II) salt.

The oxidation proceeds by a free-radical chain reaction for which NHPI acts as a radical promoter. A free-radical initiator generates phthalimido N-oxyl (PINO) radical by hydrogen abstraction from NHPI. In the propagation phase, the PINO radical abstracts a hydrogen atom from a C—H bond forming an alkyl radical R•. The alkyl radical is trapped by oxygen leading to an alkyl peroxyl radical ROO• which abstracts hydrogen atom from NHPI to form alkyl hydroperoxide ROOH.

When cobalt (II) salts are present, the initiator is thought to be Co(III)OO• radical. The alkyl hydroperoxide ROOH formed in the propagation phase is decomposed to an alkoxy radical RO• which abstracts hydrogen atom from NHPI to form an alkyl alcohol ROH.

The method has been adapted for the oxidation of primary and secondary alkyl benzenes to phenols, aldehydes and ketones as well as for the oxidation of alcohols to aldehydes and ketones, the oxidation of alkynes to ynones and for the epoxidation of alkenes (see, for example, Ishii, Y., Sakaguchi, S. and Iwahama, T. in "Innovation of Hydrocarbon Oxidation with Molecular Oxygen and Related Reactions in Advances in Synthetic Catalysis, 2001, 343, 393-427).

Aerobic oxidation (with air or oxygen) with NHPI offers an alternative method for the allylic oxidation of alkenes to enones. Such a method is of interest to industrial chemists because NHPI is non-toxic and easily prepared from phthalic anhydride and hydroxylamine.

However, the use of NHPI as a catalyst for the aerobic oxidation of alkenes to enones has not generally proved to be successful. The polarity of NHPI and its limited operating temperature range (NHPI undergoes decomposition at temperatures higher than 80° C.) means that is often necessary to use large volumes of polar solvents (which are often toxic) for a solubilization of NHPI achieving an acceptable conversion. These solvents often complicate the isolation of reaction products.

Therefore, recent methods for aerobic oxidation of alkenes to enones using NHPI are dominated by the use of co-oxidants and/or co-catalysts, such as tert-butyl hydroperoxide, and dibenzoyl peroxide, chromium (VI) salts, copper (II) salts, manganese (II) salts and complexes of cobalt (III), such as tris(acetylacetonate)cobalt (III).

These methods are not suitable for an industrial process because they use of stoichiometric amounts of NHPI and provide for only moderate conversion of alkenes with low selectivity for enone (as compared to alcohol). Further, the co-oxidants and/or co-catalysts can be explosive, difficult to remove from the crude reaction product(s) and are often toxic.

US 2004/0014985 A1 discloses one successful method for the aerobic oxidation of organic compounds using NHPI or derivatives of NHPI. The derivatives are said to enable an efficient and simple separation of reaction product from the catalyst or an altered form of the catalyst.

In the examples, an allylic oxidation of valencene to nootkatone using NHPI in combination with two or more co-catalysts consisting of cobalt (II) salt(s) and a complex of a cobalt (III) is described.

The oxidation, appears to proceed over 3 to 4 hours with reasonable conversion and selectivity for nootkatone as opposed to nootkatol, although detectable levels of nootkatol are still produced. The reaction also requires relatively high amounts of NHPI, high amounts of acetonitrile as the solvent, and an elevated temperature of 40° C., as well as the use of high pressure (1.3 MPa; 11.3 bar). Although the air flow into the reaction mixture may be provided at standard conditions, the elevated temperatures and pressures are maintained throughout the reaction.

Although the allylic oxidation is carried out on a large scale, the suitability of this method for an industrial process is limited by the requirement for two or three cobalt-containing co-catalysts and the use of high pressure and elevated temperature, and relatively large amounts of solvent.

In particular, the use of high pressure and elevated temperature on an industrial scale presents a significant risk of explosion—not least through the accumulation of hydroperoxide in the reaction mixture.

EP1164131 also discloses a method for the aerobic oxidation of organic compounds using NHPI or derivatives thereof. In an example of the oxidation of valencene to produce nootkatone, the process requires the use of relatively large amounts of NHPI and two or more co-catalysts consisting of cobalt (II) salts and a complex of cobalt (III). This process is also carried out at elevated temperatures (40° C.) for at least 4 hours. Large amounts of solvent (acetonitrile) are required, and detectable levels of nootkatol are produced. This process is therefore clearly not suitable for industrial production of α,β-unsaturated ketones.

Accordingly, there remains a need for a method of allylic oxidation of alkenes to enones which is suitable for an industrial process.

The present invention addresses that need by providing an NHPI catalyzed aerobic oxidation of alkenes to enones at standard temperature and pressure.

The method uses less NHPI and other catalyst(s) as compared to the aforementioned methods. The method may also use considerably less solvent than these methods. The method also minimizes the risk of explosion and has considerably less environmental impact as compared to other methods.

In a first aspect, therefore, the present invention provides a method for the manufacture of an α,β-unsaturated ketone, which method comprises oxidizing an unsaturated hydrocarbon having —$CH_2$— adjacent a carbon-carbon double bond (also referred to herein as "the alkene") to α,β-unsaturated ketone by passing air or oxygen through a solution of the unsaturated hydrocarbon containing a catalyst consisting of N-hydroxyphthalimide (NHPI) and cobalt diacetate tetrahydrate at standard temperature and pressure during a period of at least 12 hours.

By "standard conditions" it is meant that the reaction can be carried out without heating (or cooling), i.e. at ambient conditions ("room temperature"), and without the application of increased pressure.

References to an "unsaturated hydrocarbon having —$CH_2$— adjacent a carbon-carbon double bond" are references to a molecule containing only carbon and having a chemical structure containing one or more of the moiety >C═C—$CH_2$—, and this material is also referred to herein as "the alkene".

Although the method may be applicable to any unsaturated hydrocarbon (including alkyl benzenes and even molecules having the requisite >C═C—$CH_2$— and atoms other than carbon), in the most practical embodiments, the unsaturated hydrocarbon having —$CH_2$— adjacent a carbon-carbon double bond is an alkene having between 4 and 30 carbon atoms.

The method has particular utility for the manufacture of fragrance compounds that simply comprise α,β-unsaturated ketones—especially when the alkenes are commercially available or are readily prepared or isolated.

Accordingly, the alkene may comprise between 5 and 20 carbon atoms, for example between 8 and 20 carbon atoms. The alkene may be substituted by, for example, $C_1$-$C_5$ alkyl, $C_1$-$C_5$ alkenyl, $C_5$ or $C_6$ cycloalkyl, $C_5$ or $C_6$ cycloalkenyl or $C_6$ or $C_{10}$ aryl groups in the benzene ring or at —$CH_2$— in the alkyl group.

In certain embodiments, the alkene is a straight- or branched-chain alkene having from 4 to 20 carbon atoms and formula:

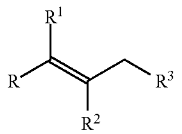

wherein:

- R, $R^1$ and $R^2$ are independently hydrogen, a $C_1$-$C_5$ straight or branched chain alkyl group, a $C_1$-$C_5$ straight or branched chain alkenyl group or $C_6$ or $C_{10}$ aryl group; and
- $R^3$ is a $C_1$-$C_5$ alkyl group, a $C_1$-$C_5$ alkenyl group or $C_6$ or $C_{10}$ aryl group.

In one such embodiment, the R and $R^3$ are each $C_6$ or $C_{10}$ aryl group and $R^1$ and $R^2$ are each hydrogen.

In other embodiments, therefore, the alkene comprises a 5- or 6-membered unsaturated carboxylic ring and has formula:

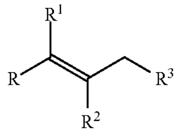

wherein:

- R is linked with $R^3$, and $R^1$ and $R^2$ are each independently hydrogen, a $C_1$-$C_5$ alkyl group, a $C_1$-$C_5$ alkenyl group or a $C_6$ or $C_{10}$ aryl group and
- the unsaturated carbocyclic ring is optionally substituted by one or more of a bridging —$CH_2$— group, a $C_1$-$C_5$ alkyl group, a $C_1$-$C_5$ alkenyl group, a $C_6$ or $C_{10}$ aryl group or fused with another 5- or 6-membered saturated carbocyclic ring which is optionally substituted by one or more of a $C_1$-$C_5$ alkyl group, a $C_1$-$C_5$ alkenyl group, a $C_6$ or $C_{10}$ aryl group; or
- R is linked with $R^3$ and $R^1$ is linked with $R^2$ to form a 5- or 6-membered saturated carbocyclic ring fused with the 5- or 6-membered unsaturated carboxylic ring; and
- one or both of the carbocyclic rings being optionally substituted by one or more a bridging —$CH_2$— group, a $C_1$-$C_5$ alkyl group, a $C_1$-$C_5$ alkenyl group or fused with another 5- or 6-membered saturated carbocyclic ring which is optionally substituted by one or more of a $C_1$-$C_5$ alkyl group, a $C_1$-$C_5$ alkenyl group, a $C_6$ or $C_{10}$ aryl group.

In these embodiments, the alkene may be a hemiterpenoid, a monoterpenoid or a sesquiterpenoid.

The alkene may, in particular, comprise any of the following cycloalkenes:

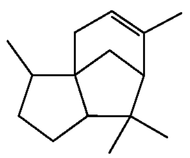
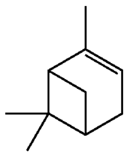
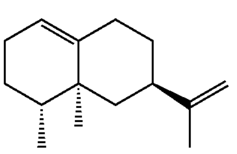

-continued

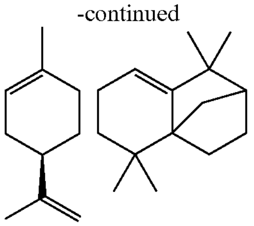

In particularly preferred embodiments of the invention the alkene is valencene.

In embodiments, the method comprises passing air (rather than oxygen) through the solution.

Although reasonable conversions of the alkene to an enone may be obtained by passing air through the solution during a period of 12 hours, good conversions may require longer.

In certain embodiments, therefore, the method may have a duration of between 12 hours and 36 hours, in particular, between 20 hours and 30 hours, and for example, 24 hours.

As noted herein, the catalyst employed in the solution of the alkene for the process of the present invention consists of NHPI and cobalt diacetate tetrahydrate. Thus, both NHPI and cobalt diacetate tetrahydrate are present in the solution, NHPI functioning as the primary catalyst and cobalt diacetate tetrahydrate functioning as a co-catalyst, and essentially no other catalysts (or co-catalysts) are present.

Advantageously, the method may employ the NHPI catalyst in an amount less than or equal to 15% mole equivalent of the alkene. Preferably the amount of NHPI used in the process of the invention is 12% mole equivalent or less, more preferably 10% mole equivalent or less.

The mole ratio of cobalt (II) acetate tetrahydrate to NHPI catalyst in the methods of the present invention is advantageously between 1:4 and 1:6, for example, about 1:5.

The solution of the alkene through which air or oxygen is passed in the present invention may be obtained by dissolving the alkene in a solvent in any convenient manner. However, whilst the allylic oxidation may be carried out in a variety of solvents, the conversion of the alkene to enone appears to be somewhat dependent on the selection of solvent. For example, the aerobic oxidation does not occur when the solvent is one or more of toluene, tetrahydrofuran, dioxane or dichloromethane. More suitable solvents will be known to the skilled person, but it should be noted that the conversion of unsaturated hydrocarbon may be low (between 20 to 30%) and/or lead to some alcohol (about 5 mol %) when the solvent is one or more of acetone, cyclohexanone, t-butanol, ethyl acetate and diethyl ether.

Further, whilst the polar solvents methyl ethyl ketone, dimethyl formamide and acetonitrile offer good conversion (near to 70%), their use may still lead to the production of alcohol (up to 5 mol %), and they also lead to difficulties in isolating α,β-unsaturated ketone by standard work-up procedures due to their partial solubility in water.

Preferably, therefore, the method of the present invention employs one or more of methyl propyl ketone (MPK), methyl isopropyl ketone (MIPK), methyl butyl ketone (MBK) and methyl isobutyl ketone (MIBK) as the solvent.

In a preferred embodiment, the method employs methyl isobutyl ketone (MIBK) as the solvent.

The method may employ solvent in an amount of from 0.75 to 9.0 liters per kilogram of the alkene, preferably from 1 to 7.5 liters per kilogram, more preferably from 1 to 6 liters per kilogram.

When methyl isobutyl ketone (MIBK) is used as solvent, the amount of solvent per kilogram of alkene may, in particular, be between 3.0 and 6.0 liters per kilogram.

The method may provide a conversion of the alkene to α,β-unsaturated ketone of greater than or equal to 65%, for example, greater than or equal to 70%. The conversion of alkene may, for example, be monitored by gas chromatography and the oxidation quenched when a desired conversion is obtained. Alternatively, the oxidation may be quenched after a predetermined time period, for example, 24 hours has elapsed.

The method may provide an allylic oxidation of alkene that is highly selective for α,β-unsaturated ketone (as compared to the alcohol). In other words, the α,β-unsaturated ketone is obtained substantially free from the corresponding alcohol. By "substantially free" from the corresponding alcohol, it is meant that less than 1% by weight (% w/w) is produced. In preferred embodiments of the invention, the amount of alcohol produced is less than 0.5% w/w, and most preferably essentially no alcohol is produced, i.e. no alcohol can be detected using conventional testing procedures.

The method may also provide an allylic oxidation having regioselectivity between 95% and 100%. In other words, the method provides substantially one α,β-unsaturated ketone when the unsaturated hydrocarbon comprises two or more —$CH_2$— adjacent a carbon-carbon double bond.

The method does not require any special measures for the work up of the reaction mixture. Nor does it require the derivatives of NHPI mentioned in US 2004/0014985 A1—although it is envisaged that these derivatives might be used in place of NHPI.

In embodiments, therefore, the method further comprises quenching the oxidation by water, extracting the α,β-unsaturated ketone into an organic solvent and washing the extract with 5 wt/wt % aqueous sodium hydroxide.

As mentioned above, the method is particularly suitable for the manufacture of fragrance compounds comprising α,β-unsaturated ketones.

The method provides at least the following fragrance compounds in good yields (70% or more) with 100% regioselectivity:

Verbenona

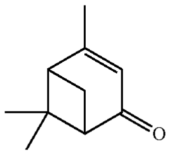

Isolongifolenona

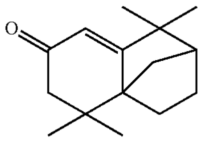

Carvona

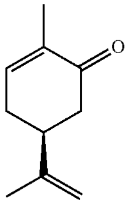

-continued

Nootkatone

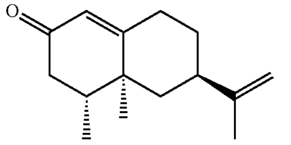

Cedrenona

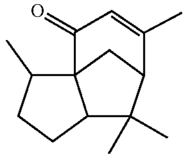

In a preferred embodiment, the fragrance compound produced is nootkatone.

In an embodiment of the present invention, the method is adapted for manufacture of the α,β-unsaturated ketone on an industrial scale. By "industrial scale" it is meant that the α,β-unsaturated ketone is produced in a sufficient amount for industrial use, i.e. large enough amounts are produced to make the process commercially viable and to satisfy demand for the product cost effectively.

In a second aspect therefore, the present invention provides an industrial process for the manufacture of an α,β-unsaturated ketone according to the method of the first aspect. By an "industrial process" it is meant that the process is carried out at a commercially viable scale, with an acceptable level of safety and cost considerations, and can produce the product on a scale as indicated above.

Embodiments in this aspect will be apparent from the foregoing description relating to the first aspect of the present invention.

In a third aspect, the present invention provides an industrial installation for manufacture of an α,β-unsaturated ketone according to the method of the first aspect. It will be understood that an industrial installation is an installation adapted to produce an end product or products on an industrial scale, as defined herein.

Suitable apparatus for the industrial installation will be apparent to those skilled in the art when considered with the first aspect of the present invention.

Figure 2:
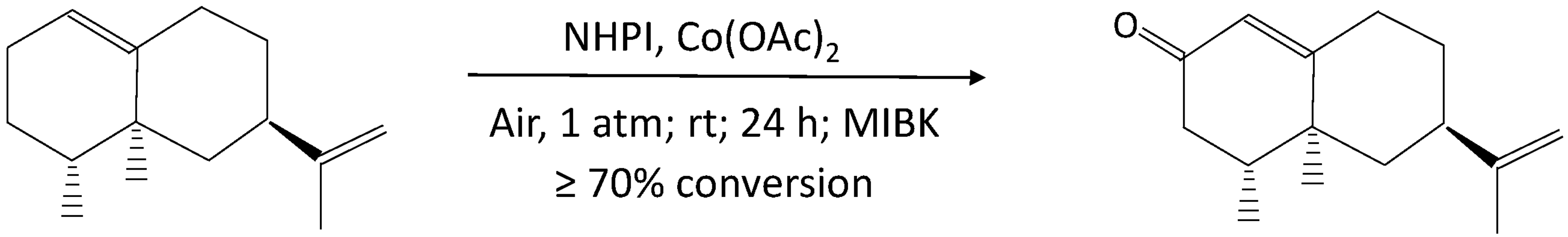

The present invention will now be described in more detail with reference to the following non-limiting Examples and the accompanying drawings in which:

FIG. 1 is a scheme generally illustrating the chemical transformation of allylic oxidation of an alkene to an α,β-unsaturated ketone; and FIG. 2 is a scheme illustrating aerobic oxidation of an alkene to an α,β-unsaturated ketone according to one embodiment of the present invention.

Referring now to FIG. 1, there is shown the allylic oxidation of an alkene having $—CH_2—$ adjacent a carbon-carbon double bond to an α,β-unsaturated ketone ($R^3$ is an alkyl or aryl group). As may be seen, the allylic oxidation comprises a chemical transformation of the alkene providing for substitution of the two hydrogen atoms of the $—CH_2—$ adjacent the carbon-carbon double bond by a carbon-oxygen double bond.

The allylic oxidation is shown as being brought about by an aerobic oxidation over at least ten hours of a solution of the alkene using air and a catalyst comprising a mixture of NHPI and cobalt (II) acetate tetrahydrate without heating, i.e., at room temperature and at atmospheric pressure (viz., at standard temperature and pressure (STP)).

Referring now to FIG. 2, a similar aerobic oxidation is applied to the synthesis of the fragrance compound Nootkatone from Valencene (a sesquiterpene which is inexpensively obtained from Valencia oranges).

The synthesis of Nootkatone is achieved by an aerobic oxidation over twenty four hours of a solution of the alkene in methyl isobutyl ketone (MIBK) using air and a catalyst comprising a mixture of NHPI and cobalt (II) acetate tetrahydrate at room temperature and at atmospheric pressure (viz., at standard temperature and pressure (STP)).

The synthesis on laboratory and pilot plant scale is described in the following examples. In each case, the production of Nootkatone (and the absence of Nootkatol) was confirmed by $^1$H and $^{13}$C NMR spectroscopy with reference to library NMR spectra for Nootkatone.

EXAMPLE 1

Laboratory Scale

A stream of air was introduced into a stirred solution of N-hydroxyphthalimide (1.76 g, 0.01 mol, 0.1 eq), $Co(OAc)_2$ (0.58 g, 0.002 mol, 0.025 eq.) and (+)-valencene (20 g, 0.1 mol, 1 eq) in methyl isobutyl ketone (MIBK, 120 mL, f=6) in a 250 mL round-bottom flask at room temperature during a period of 24 hours and at a flow rate sufficient to create microbubbles.

The reaction was monitored by gas chromatography of aliquots of the solution to evaluate the conversion of (+)-valencene to (+)-nootkatone and the reaction quenched when the conversion reached the 70%. After removal of the air stream, the reaction mixture was washed twice with 50 ml of distilled water followed by once with 50 ml of 5% aqueous sodium hydroxide. The presence of nootkatone was confirmed by $^1$H and $^{13}$C NMR spectroscopy, and no nootkatol was detected.

EXAMPLE 2

Pilot Plant Scale

A stream of air was introduced into a stirred solution of N-hydroxyphthalimide (87.81 g, 0.489 mol, 0.1 eq), $Co(OAc)_2$ (29.5 g, 0.108 mol, 0.022 eq.) and (+)-valencene (1000 g, 4.89 mol, 1 eq) in methyl isobutyl ketone (MIBK, 3000 mL, f=3) in a 10 liter reactor at room temperature during a period of 24 hours and at a flow rate creating microbubbles.

The reaction was monitored by gas chromatography of aliquots of the solution to evaluate the conversion of (+)-valencene to (+)-nootkatone and the reaction quenched when the conversion reached 70%. After removal of the air stream, the reaction mixture was washed twice with 1000 ml of distilled water followed by one with 750 ml of 5% aqueous sodium hydroxide.

After removal of the MIBK solvent by vacuum distillation, rectification gave 694 g (65%) nootkatone. The (+)-nootkatone had 95% purity and was determined to be free from (+)-nootkatol.

It will be seen, therefore, that the present invention provides a method for the aerobic oxidation of alkenes to α,β-unsaturated ketones which is suitable to industrial scale. The method does not require oxygen or heating, and is carried out at atmospheric pressure so mitigating the risk of explosion and minimizing energy consumption as compared to the aforementioned methods.

The method uses less catalyst (in number and amount) as compared to the aforementioned methods and may use less solvent. It offers high conversion of alkene to α,β-unsaturated ketone and is highly selective and highly regioselective.

Low catalyst, low solvent, minimized energy consumption and high conversion, selectivity and regioselectivity mean that the method is highly suitable for use as a green (environmentally friendly) industrial process for the manufacture of fragrance compounds comprising α,β-unsaturated ketone.

The invention claimed is:

1. A method for the manufacture of an α,β-unsaturated ketone, which method comprises oxidizing an unsaturated hydrocarbon having —CH2- adjacent a carbon-carbon double bond ("the alkene"), wherein the alkene is selected from the group of compounds consisting of:

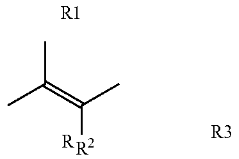

to α,β-unsaturated ketone by passing air or oxygen through a solution of the alkene containing a catalyst consisting of N hydroxyphthalimide (NHPI) and cobalt diacetate tetrahydrate, wherein the mole ratio of cobalt diacetate tetrahydrate to NHPI catalyst is from 1:4 to 1:6 and wherein the amount of NHPI catalyst is less than 15% mole equivalent of the alkene in solvent comprising one or more of methyl propyl ketone (MPK), methyl isopropyl ketone (MIPK), methyl butyl ketone (MBK) and methyl isobutyl ketone (MIBK) at standard temperature and pressure during a period of at least 12 hours.

2. A method according to claim 1, comprising passing air through the solution at standard temperature and pressure during a period of at least 12 hours.

3. A method according to claim 1, wherein the alkene has between 4 and 30 carbon atoms.

4. A method according to claim 1, wherein the alkene is a hemiterpenoid, a monoterpenoid or a sesquiterpenoid.

5. A method according to claim 1, wherein the alkene is valencene.

6. A method according to claim 1, wherein an amount of solvent from 0.75 to 9.0 liters per kilogram of the alkene is used.

7. A method according to claim 1, providing a conversion of the alkene greater than or equal to 70%.

8. A method according to claim 1, providing the α,β-unsaturated ketone substantially free from the corresponding alcohol.

9. A method according to claim 1, having a regioselectivity greater than 95%.

10. A method according to claim 1, further comprising quenching by water, extracting the α,β-unsaturated ketone into an organic solvent and washing the extract with 5 wt/wt % aqueous sodium hydroxide.

11. A method according to claim 1, wherein the α,β-unsaturated ketone is a fragrance compound.

12. A method according to claim 11, wherein the α,β-unsaturated ketone is nootkatone.

13. A method according to claim 1, adapted for manufacture of the α,β-unsaturated ketone on an industrial scale.

* * * * *